United States Patent [19]

Steinert

[11] Patent Number: 5,215,104
[45] Date of Patent: Jun. 1, 1993

[54] METHOD FOR CORNEAL MODIFICATION

[76] Inventor: Roger F. Steinert, 83 Sandra La., North Andover, Mass. 01845

[21] Appl. No.: 655,431
[22] PCT Filed: Aug. 14, 1989
[86] PCT No.: PCT/US89/03501
   § 371 Date: Mar. 20, 1991
   § 102(e) Date: Mar. 20, 1991

Related U.S. Application Data

[63] Continuation of Ser. No. 232,788, Aug. 16, 1988, abandoned.

[51] Int. Cl.⁵ .............................................. A61B 17/32
[52] U.S. Cl. ........................................ 128/898; 606/5; 606/166
[58] Field of Search .................... 128/898; 604/22; 606/166, 161, 5

[56] References Cited

U.S. PATENT DOCUMENTS

| | | | |
|---|---|---|---|
| 2,192,699 | 3/1940 | Storz | 128/305 |
| 3,809,092 | 5/1974 | Abraham | 128/305 |
| 3,908,661 | 9/1975 | Kramer | 128/305 |
| 3,943,931 | 3/1976 | Krasnov | 128/303.1 |
| 4,024,866 | 5/1977 | Wallach | 128/276 |
| 4,173,980 | 11/1979 | Curtin | 128/303 R |
| 4,205,682 | 6/1980 | Crock et al. | 128/305 |
| 4,298,004 | 11/1981 | Schachar et al. | 128/305 |
| 4,452,235 | 6/1984 | Reynolds | 128/1 R |
| 4,481,948 | 11/1984 | Sole | 128/303.14 |
| 4,538,611 | 9/1985 | Kelman | 128/305 |
| 4,558,698 | 12/1985 | O'Dell | 128/303.1 |
| 4,607,617 | 8/1986 | Choyce | 128/1 R |
| 4,610,248 | 9/1986 | Rosenberg . | |
| 4,655,774 | 4/1987 | Choyce | 623/5 |
| 4,660,556 | 4/1987 | Swinger et al. | 128/305 |
| 4,662,881 | 5/1987 | Nordan | 623/5 |

FOREIGN PATENT DOCUMENTS

| | | | |
|---|---|---|---|
| 3433581 | 3/1986 | Fed. Rep. of Germany | 128/305 |
| 519191 | 8/1976 | U.S.S.R. | 128/305 |

OTHER PUBLICATIONS

C. A. Swinger et al., "Planar Lamellar Refractive Keratoplasty", Journal of Refractive Sergery, vol. 2, 1986, pp. 17-24.
T. Krwawicz, "Lamellar Corneal Stromectomy", Notes, Cases, Instruments, pp. 828-833, Am. J. Ophth 1964; 57.
R. L. Lindstrom et al., "Ploysulfone Intracorneal Lenses", Ch. 27, in D. R. Sanders et al., eds. Refractive Corneal Surgery, Slack Inc., N.J., 1986, pp. 551-563.
C. A. Swinger, Chapter 23 in D. R. Sanders et al., eds., Refractive Corneal Surgery, SLACK, Inc. N.J., 1986, pp. 469-493.
M. B. MacDonald et al., Chapter 21 in D. R. Sanders et al., eds., Refractive Corneal Surgery, SLACK Inc., N.J., 1986, pp. 427-448.

Primary Examiner—Michael H. Thaler
Attorney, Agent, or Firm—Fish & Richardson

[57] ABSTRACT

Method and apparatus for surgically altering the cornea of an eye by forming a pocket in the corneal stroma, situated between anterior posterior lamellar portions of the cornea, posteriorly displacing the anterior corneal portion to form a posteriorly protruding mass of corneal stroma, excising a part of the posteriorly protruding mass, and removing the excised part from the pocket. Also, the invention includes inserting into the pocket a die that has an anteriorly facing impression surface whereby posteriorly displacing the anterior lamellar portion forces a portion of the posteriorly protruding mass against a portion of the impression surface, and further includes removing the die from the pocket after the excision. Also, apparatus for surgically modifying the cornea of an eye includes a cutter guide for placement in a pocket formed in the corneal stroma, adapted to be placed between anterior and posterior lamellar portions of the cornea, and a cutter for excising a posterior portion of the posterior stromal mass of the anterior lamellar portion, the cutter and the guide being adapted to cooperate in guiding the cutter through a prescribed effective stroke during the excision. Also, the apparatus includes a die for placement in a pocket formed in the corneal stroma between anterior and posterior lamellar portions of the cornea, and a cutter for excising a posterior portion of the posterior stromal mass.

47 Claims, 8 Drawing Sheets

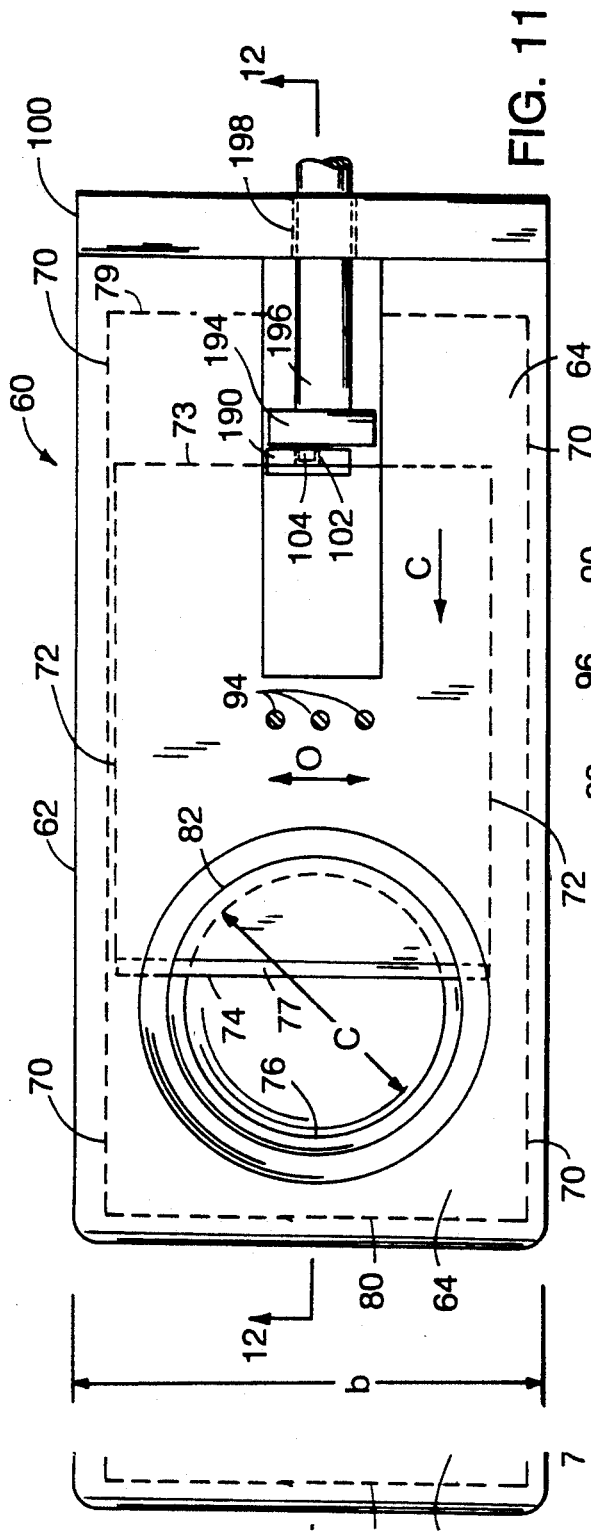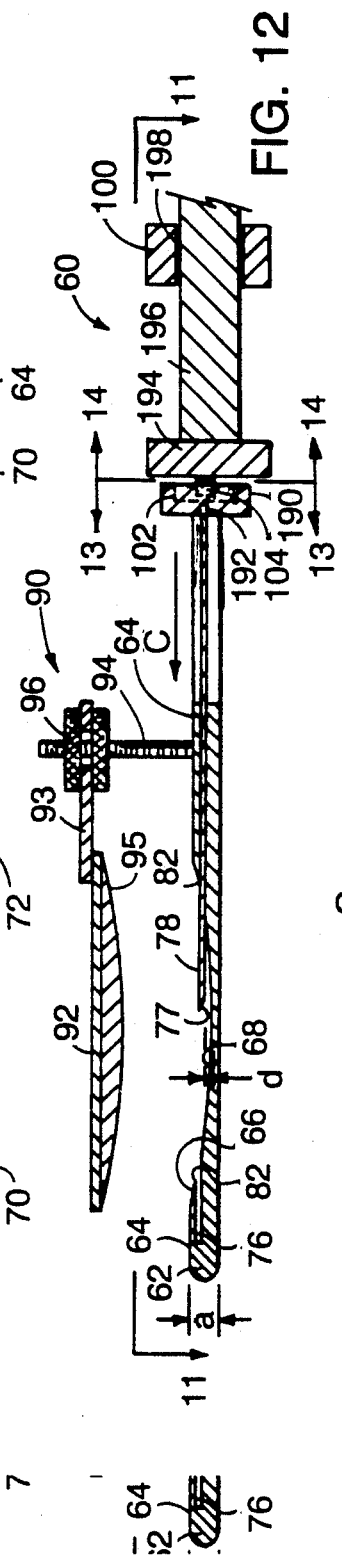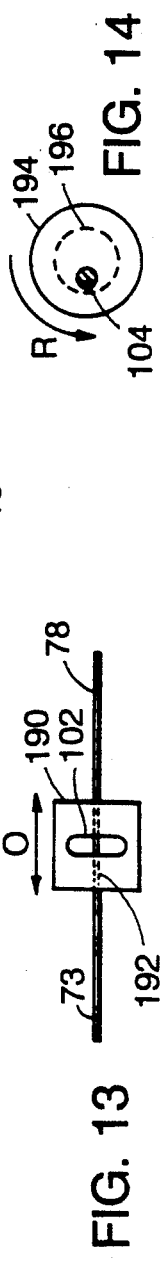

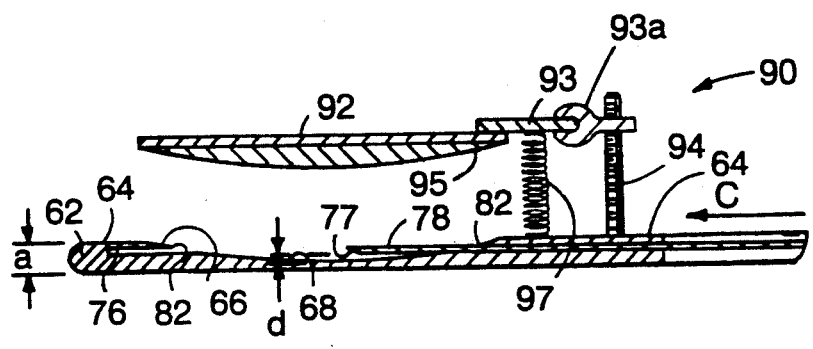
FIG. 12a
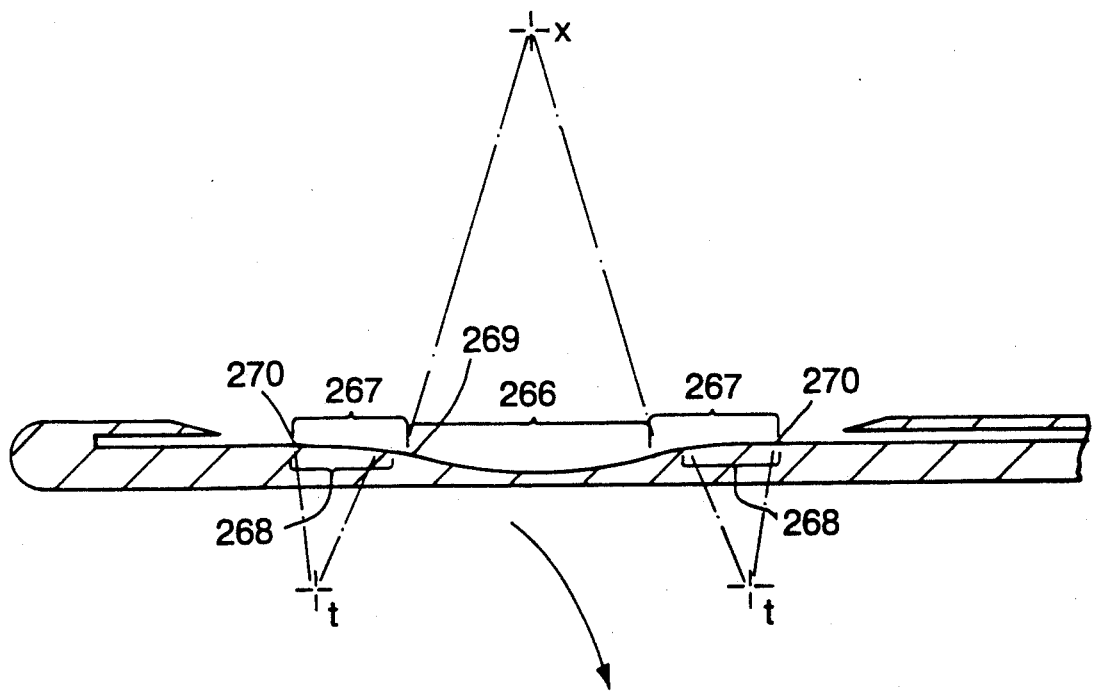
FIG. 19
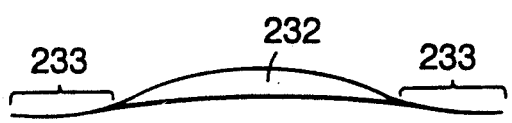

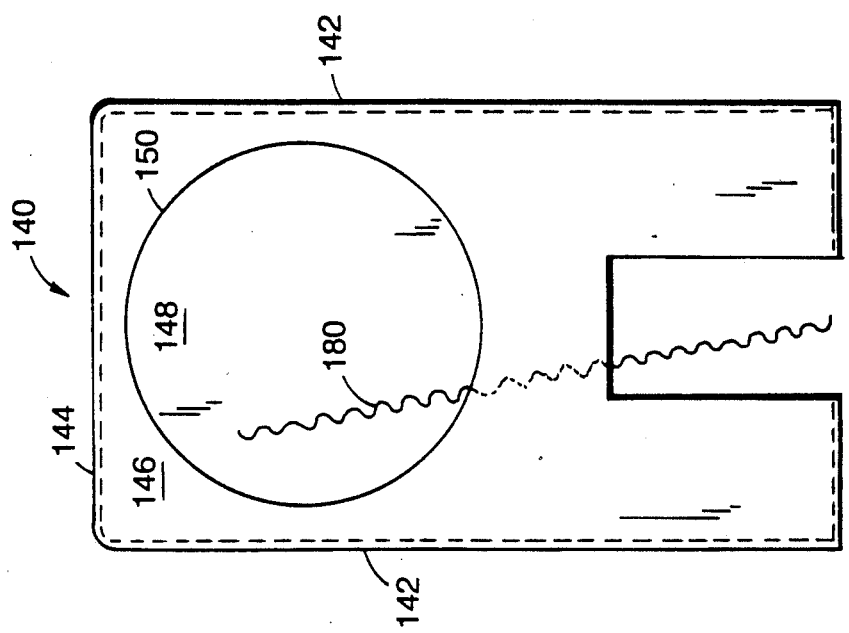
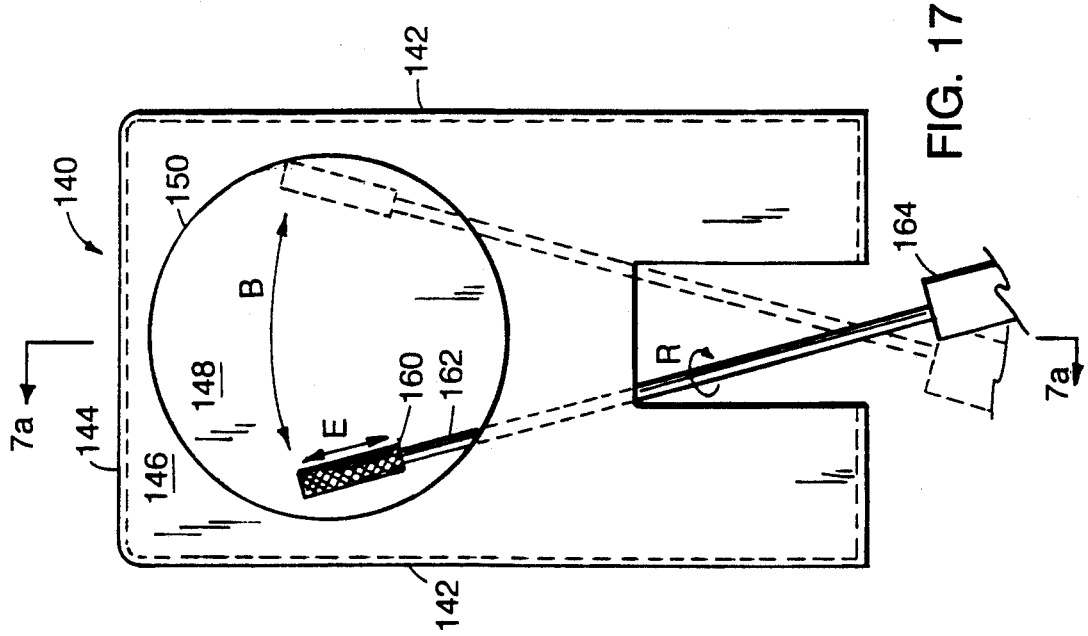

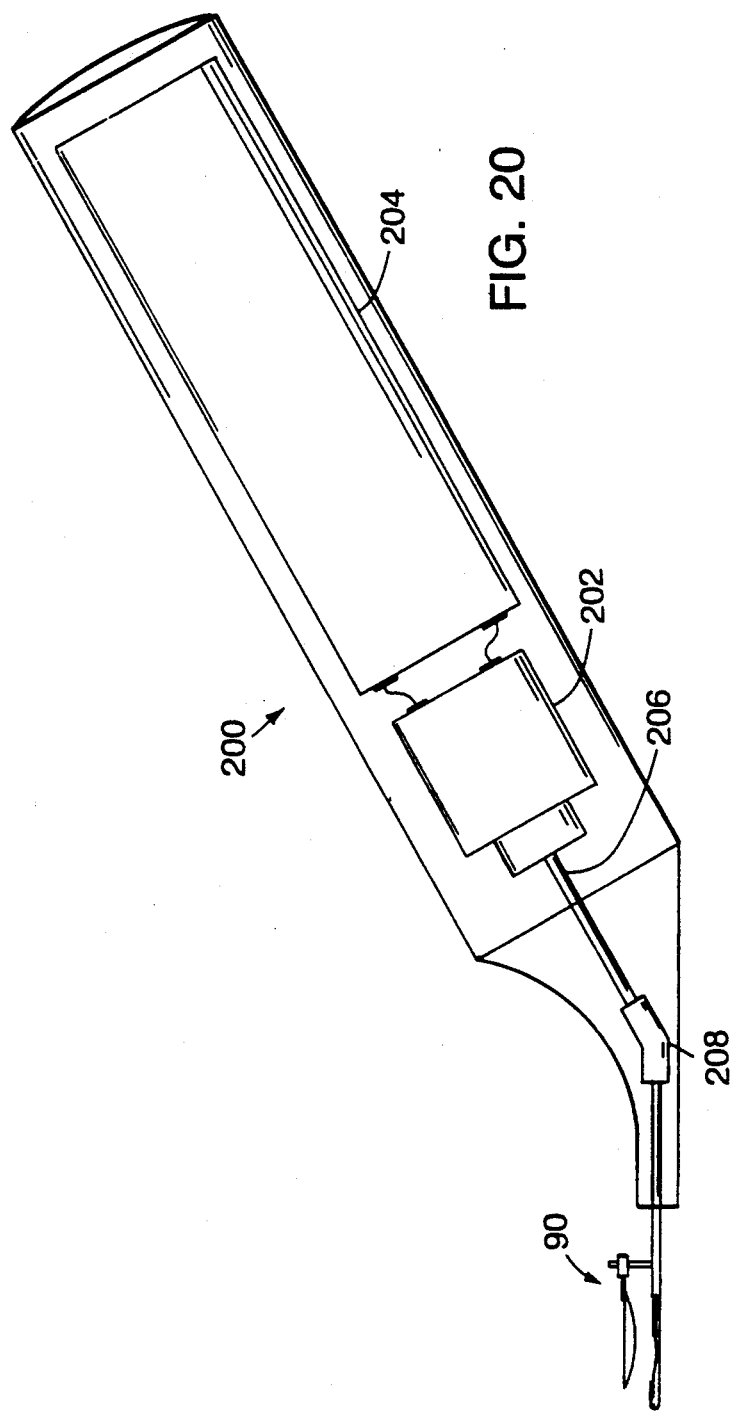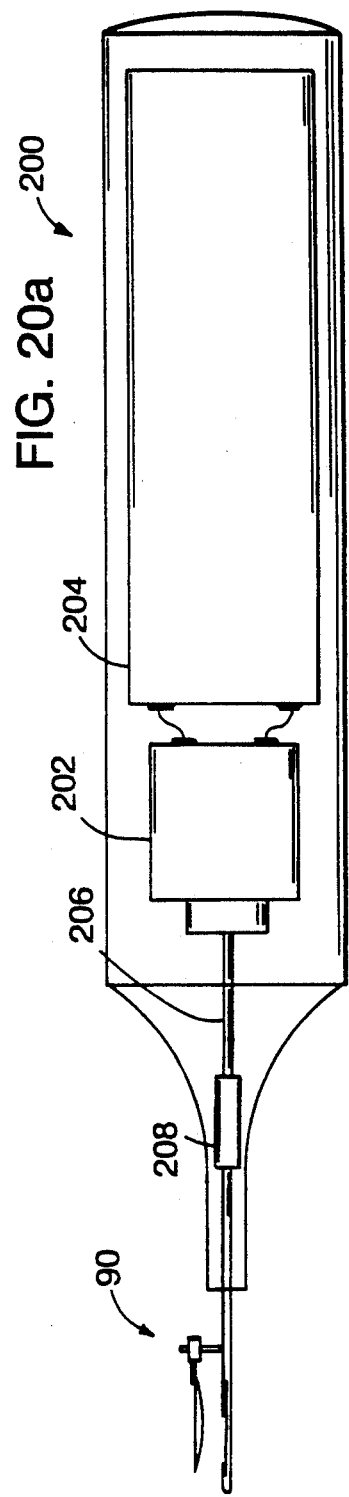

METHOD FOR CORNEAL MODIFICATION

This application is a continuation of U.S. patent application Ser. No. 232,788, filed Aug. 16, 1988, now abandoned, and based upon the intervening Patent Cooperation Treaty application PCT/US89/03501 filed Aug. 14, 1989 which claimed priority therefrom.

BACKGROUND OF THE INVENTION

This invention relates to surgical alteration of the cornea of the eye.

The cornea, the transparent dome-shaped anterior portion of the fibrous covering of the eye, comprises several layers. The anterior surface includes the corneal epithelium, consisting of several layers of cells covering the front of the cornea. The posterior surface includes a corneal endothelium, consisting of a layer of cells. Between the corneal epithelium and the corneal endothelium is the corneal stroma, or substantia propria corneae, composed of about 60 superimposed connective tissue lamellae held together in placed by an interstitial cement substance and separated in other places by corneal spaces containing corneal corpuscles. The stroma is bounded anteriorly by the anterior lamina, also termed Bowman's membrane, consisting of closely interwoven fibrils, and posteriorly by the posterior elastic lamina, also termed the membrane of Descemet. In the average human eye the cornea is a part-spherical body about 0.5 mm thick over most of its extent; the stroma itself comprises about 90% of the total corneal thickness.

The cornea contributes a majority of the refractive power of the human eye, and for this reason surgical alteration of the shape of the cornea, often termed "keratoplasty", can result in significant changes in the refractive characteristic of the eye. Techniques of refractive keratoplasty can be classified as keratotomy, by which the curvature of the cornea is altered generally and the thickness is not substantially altered; or as lamellar refractive keratoplasty, by which the curvature of only the anterior surface of the cornea is altered, and the cornea is made thicker or thinner over some of its extent.

Known techniques of lamellar keratoplasty in which the anterior curvature of the cornea is altered include the classic Barraquer technique, in which a portion of the cornea is removed, reshaped and surgically replaced. In this technique a lamellar corneal disc, comprising the anterior surface and some stromal matter, is removed from an eye and positioned on a plastic holder with one surface of the corneal disc against a part-spherical cavity in the holder; then the corneal disc is frozen in the cavity and a part-spherical surface is cut from the other surface of the corneal disc using a cryolathe; and finally the resulting lenticule is thawed, replaced on the cornea and sutured in place. Where the part-spherical surface cut from the corneal disc has a raduis of curvature greater than that of the cavity in the plastic holder, the resulting lenticule is thicker near its center than near its margin; when such a lenticule is grafted onto a cornea of a hyperopic eye, it imparts a steeper curvature to the anterior surface, correcting the hyperopia. Conversely, where the part-spherical surface cut from the corneal disc has a raduis of curvature less than that of the cavity in the plastic holder, the resulting lenticule is thinner near its center than near its margin; when such a lenticule is grafted onto a cornea of a myopic eye, it imparts a flatter curvature to the anterior surface, correcting the myopia.

C. A. Swinger et al., 1986, Jour. Refractive Surgery, Vol. 2, pp. 17-24, describes a variation of the classic Barraquer technique, in which the epithelial surface of the corneal disc is placed onto the base upon a die surface whose curvature is selected according to the type and degree of correction required. Material is then removed from the corneal disc by making a planar cut through the disc using a microkeratome, and the resulting lenticule is replaced on the cornea and sutured in place.

T. Krwawicz, 1964, Am. Jour. Ophthalmol., Vol. 57, pp. 828-33, describes altering corneal curvature for correcting human myopia by a technique in which a thin lamella of the stroma is removed from the central part of the cornea for changing its curvature to modify the refraction of the eye. Krwawicz's technique consists of making an anterior incision into the cornea near the margin of a circular operating area, not going beyond the superficial layers of the stroma; splitting the stroma in two planes parallel to the anterior and posterior surfaces; and excising the resulting lamellar flap with a punch forceps.

SUMMARY OF THE INVENTION

In general, in one aspect, the invention features a method and apparatus for surgically altering the cornea of an eye by substraction of tissue in situ, by forming a pocket in the corneal stroma between an anterior lamellar portion and a posterior lamellar portion of the cornea, posteriorly displacing the anterior lamellar portion to form a posteriorly protruding mass of corneal stroma of the anterior lamellar portion, excising a part of the posteriorly protruding mass, and removing the excised part of the posteriorly protruding mass from the pocket.

In preferred embodiments, the pocket is formed by making an incision, preferably a peripheral chordal incision, in the cornea and separating the anterior lamellar portion from the posterior lamellar portion by dissection; the excision includes passing a cutter through the posteriorly protruding mass of corneal stroma; the cutter is adapted to make a straight cut, which preferably describes a plane during its passage through the posteriorly protruding mass of corneal stroma. In certain embodiments the cutter is a mechanical element which oscillates substantially in the plane of passage through the posteriorly protruding mass of corneal stroma; the element comprises a cutting edge; the edge is a gem stone blade; alternatively, the cutter comprises a length of wire under tension; the wire moves in a direction along its length as it passes through the posteriorly protruding mass of corneal stroma; and the wire is configured in a continuous loop. In other embodiments, the cutter comprises a rotating burr and the cutter comprises a laser beam; the method further includes inserting a cutter guide into the pocket before the excision, and removing the cutter guide from the pocket after the excision; the method further includes inserting into the pocket before the excision a die having an impression surface facing anteriorly when it is so inserted, so that posteriorly displacing the anterior lamellar portion of the cornea forces a portion of the posteriorly protruding mass against a portion of the impression surface, and removing the die from the pocket after the excision; the die includes the cutter guide; and the impression surface includes a part-spherical surface whose center of curvature is located anterior to, or is located posterior to, the impression surface when the die is inserted into the pocket.

In another aspect, the invention features a method for surgically altering the cornea of an eye, including forming a pocket in the corneal stroma between an anterior and a posterior lamellar portion of the cornea, inserting into the pocket a die having an impression surface that faces anteriorly when the die is inserted into the pocket, forcing a posterior portion of the stromal mass of the anterior lamellar portion against a portion of the impression surface in the die, excising a posterior part of the posterior portion of the stromal mass, and removing the die and the excised part from the pocket.

The invention provides a straightforward method for altering the anterior curvature of the cornea to a prescribed degree in a manner not requiring that the cornea be removed from the eye and replaced. As one advantage, it can be implemented with simple planar motion of a blade. Except for a relatively short incision in the peripheral cornea, the method will leave the corneal surface, including the anterior epithelium and Bowman's membrane, undisturbed. Scar formation will be limited, as will be any tendency of the cornea to respond in a healing fashion. Immediately postoperatively the corneal tissue will be optically clear and there will be no devitalized tissues that require a long period of healing. For correction of myopia, the invention provides for precisely reducing the corneal thickness near the optical axis relative to the thickness more peripherally to reduce the effective optical power of the cornea, by subtraction of tissue, that is, by removal of stromal material, without disrupting the anterior or posterior corneal membranes near the optical axis. The contour of the resulting optically corrected cornea has a simple curvature, and includes no multiple curves. For correction of hyperopia, the invention provides for precisely increasing the relative corneal thickness near the optical axis, not by addition of donor corneal material near the optical axis, as in conventional corneal surgery for hyperopia, but by removal of stromal material more peripherally. The invention avoids the need for a donor, as well as the possibility of graft rejection by the patient, and substantially reduces the likelihood of infection resulting from the procedure.

In another aspect, the invention features apparatus for surgically modifying the cornea of an eye, including a cutter guide adapted to be placed in a pocket formed in the corneal stroma between an anterior lamellar portion and a posterior lamellar portion of the cornea, and a cutter for excising a posterior portion of the posterior stromal mass of the anterior lamellar portion, the cutter and the guide being adapted to cooperate in guiding the cutter through a prescribed effective stroke during the excision. In preferred embodiments the cutter guide is adapted to receive the cutter and to direct the cutter during its effective stroke along the cutter guide in a direction toward a leading edge of the cutter guide, that is, in a direction from outside the pocket and across the optical axis of the eye; the cutter guide is adapted to prevent passage of the cutter beyond the peripheral edge of the cutter guide, to prevent the cutter from contacting the surrounding stroma. Thus the cutter enters the stromal pocket by way of the same peripheral chordal incision through which the die or the guide enters the pocket, which has no other opening through the anterior membrane of the cornea; as a result, disruptions of the anterior corneal surface are minimized, reducing the likelihood of infection and the adverse effects of the healing process.

In another aspect, the invention features apparatus for surgically modifying the cornea of an eye, including a die adapted to be placed in a pocket formed in the corneal stroma between an anterior lamellar portion and a posterior lamellar portion of the cornea, and a cutter for excising a posterior portion of the posterior stromal mass of the anterior lamellar portion.

In preferred embodiments, an insertable portion of the die is arranged and adapted to be inserted into the stromal pocket by way of an incision in the cornea, including a generally planar first die surface having a peripheral die edge, including a leading die edge region adapted to be the region of the die edge first inserted into and last removed from the pocket; the die surface lies in a plane generally perpendicular to the optical axis of the eye when the insertable portion has been placed in the pocket, and a portion of the first die surface includes an impression surface arranged to face anteriorly when the die is inserted; the impression surface is adapted to be contacted by and provide a desired shape to the posterior side of the lamellar portion; the impression surface includes a part-spherical surface, an aspherical surface, or a plurality of part-sherical surfaces whose centers of curvature are located anterior to said impression surface when said die is inserted into said pocket.

In other preferred embodiments, the die includes the cutter guide; the cutter includes a preferably straight cutting edge; the cutter guide and the cutting edge are adapted to cooperate so that the cutting edge describes a plane during its passage through the posteriorly protruding mass of corneal stroma; the cutting edge is adapted to oscillate substantially in the plane of passage through the posteriorly protruding mass of corneal stroma; the cutter includes a length of wire under tension; the wire moves in a direction along its length as it passes through the posteriorly protruding mass of corneal stroma; the wire is configured in a continuous loop; the cutter includes a rotating burr; and the cutter includes laser energy.

In each embodiment, all the insertable portion of the apparatus, whether it comprises a cutter alone or a cutter together with a die or with a cutter guide, or with a die including a cutter guide, has a cantilever configuration, the projecting end of which is constructed and arranged to be inserted in the pocket, is inserted by way of a single incision in the peripheral anterior surface of the cornea, and the cutter is operated from near the base of the cantilever.

The cutter guide ensures control of the motion of the cutter so that the prescribed portion of the posterior stromal mass of the anterior lamellar portion of the cornea is removed during excision. Inserting a selected die having a prescribed impression surface within an intrastromal pocket behind an anterior lamellar portion of the cornea and forcing the posterior stromal mass of the anterior lamina into the impression surface ensures that the resulting anterior lamina will have the prescribed shape following truncation of the posterior stromal mass. By using dies having impression surfaces of various shapes, a variety of kinds and degrees of corrections can be made, including corrections for myopia, hyperopia, and astigmatism, as well as severe hyperopia resulting from aphakia. A particular advantage of the invention for correction of myopia is that it provides for reducing the thickness of the cornea near the optical axis by removing a precisely dimensioned portion of corneal stroma without disrupting the integrity of the anterior or posterior membranes of the cornea, while preserving a natural curvature on the anterior corneal surface.

Preferably, the insertable portion of the apparatus is configured and dimensioned such that damage to stromal tissues during insertion, excision, and removal is minimized. In preferred embodiments at least a portion of the peripheral die edge is rounded; the die further includes a second generally planar die surface, generally parallel to the first die surface, and the anterior-posterior thickness of the die, as measured between the generally parallel surfaces, is in the range 0.3 mm to 3 mm, more preferably about 1 mm; the maximum width dimension of the insertable portion is in the range 3 mm to 8 mm, more preferably in the range 4 to 6 mm.

In still other preferred embodiments, a portion of the margin of the pressure surface of the pressure member extends radially beyond the margin of the impression surface of the die; the pressure member is configured to yield to displacement of the stromal mass during passage of the cutter; the pressure surface is made of a yielding material; the yielding material includes a captured gel, a membrane enclosed fluid, or cellular foam.

In other preferred embodiments, the apparatus further includes a handle; the handle includes a hollow shell, and the apparatus further includes a motor, contained within the handle, coupled to the cutter to advance the cutter through its effective cutting stroke.

DESCRIPTION OF THE PREFERRED EMBODIMENTS DRAWINGS

FIGS. 1-5 are sectional views showing steps in the method of the invention for altering corneal curvature.

FIGS. 6-7 are sectional views showing steps in the method for altering corneal curvature using an intrastromal die of the invention.

FIGS. 8-10 are sectional views showing steps in the method for altering corneal curvature using an intrastromal die having an alternative impression surface.

FIG. 11 is a sectional plan view thru XI—XI in FIG. 12 of apparatus for altering corneal curvature according to the invention.

FIG. 12 is a section thru the apparatus at XII—XII in FIG. 11.

FIG. 12a is a section thru an alternative embodiment of apparatus according to the invention, taken generally as in FIG. 12.

FIG. 13 is a section thru the apparatus at XIII—XIII in FIG. 12.

FIG. 14 is a section thru the apparatus at XIV—XIV in FIG. 12.

FIGS. 15-18 show alternative cutters and cutter guides of the invention.

FIG. 19 is a diagrammatic section view through a portion of a die, showing an alternatively configured impression surface.

FIGS. 20, 20a are plan views of the apparatus of FIG. 12, showing a handle, adapted to contain a motor for driving the cutter, in flat and angled configurations.

The drawings are not drawn to scale, and some dimensions are disproportionately represented for illustration.

One skilled in the art of ophthalmic surgery will appreciate that in the description that follows, outlining the method of the invention, many details of standard surgical practice are omitted.

Figure 1:
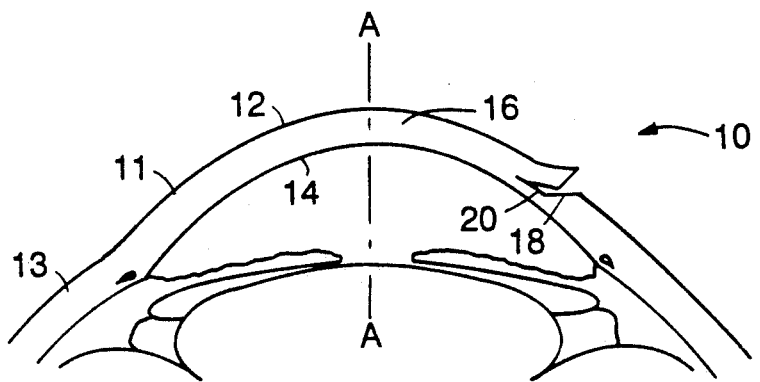
FIGS. 1-10 show anterior parts of the eye in sectional views through the optical axis of the eye.

FIG. 1 shows generally at 10 the anterior part of an eye in section thru the optical axis A—A. The cornea 11 is a part-spherical dome-shaped transparent body projecting anteriorly beyond the sclera 13 of the eyeball. Cornea 11 has an anterior corneal surface 12 (toward the exterior of the eyeball) that includes the corneal epithelium underlain posteriorly by Bowman's membrane, a posterior corneal surface 14 (toward the interior of the eyeball) that includes the corneal endothelium underlain anteriorly by the membrane of Descemet, and corneal stroma 16 situated between anterior corneal surface 12 and posterior corneal surface 14.

Figure 2:
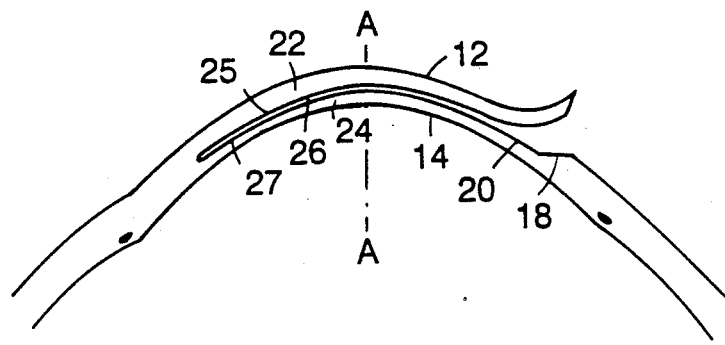

As is shown diagramatically in FIG. 1, a corneal incision 18, preferably a peripheral chordal incision, is made at a location spaced from axis A—A, passing through anterior corneal surface 12 into corneal stroma 16 to a depth 20. Then the corneal lamellae are separated at depth 20 by dissection across axis A—A, as shown in FIG. 2, to define an anterior lamellar portion of the cornea 22 and a posterior lamellar portion of the cornea 24, bounded by intrastromal pocket 26 which is situated substantially parallel to anterior and posterior corneal surfaces 12, 14 at substantially uniform corneal depth. Depth 20 of incision 18 is selected so that dissection at depth 20 to form pocket 26 will not disrupt the Bowman's membrane anteriorly or the membrane of Descemet posteriorly. An incision depth between 20% and 80% of the corneal thickness can generally suffice to provide a margin of safety. The resulting anterior and posterior lamellar portions 22, 24 have a substantially uniform thickness over much of their extent.

Figure 3:
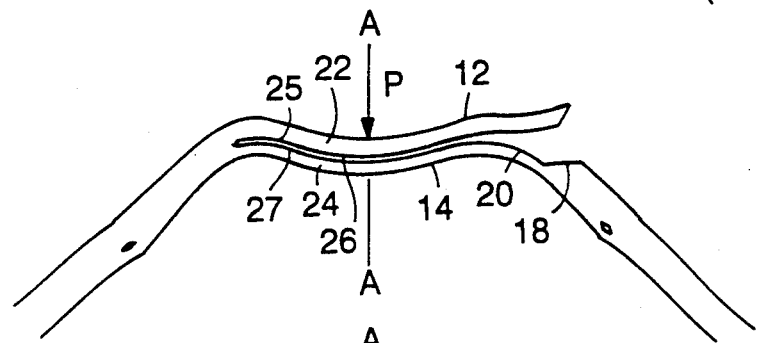
Figure 4:
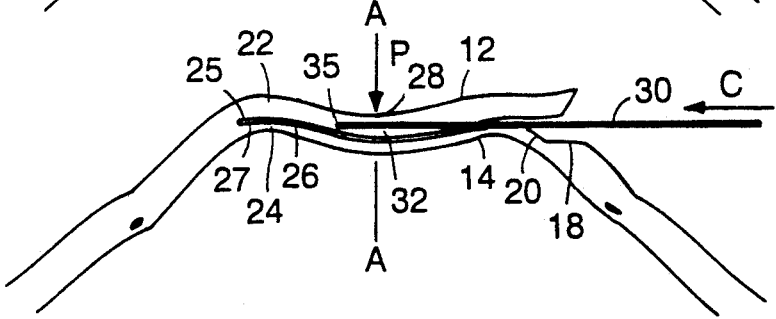

With reference to FIG. 3, substantially posteriorly directed, controlled pressure is then applied to anterior corneal surface 12 near optical axis A—A as shown generally by arrow P so as to displace lamellar portions 22, 24 to the degree desired. As a result, the curvature of the corneal lamellar portions 22, 24 can be altered to a posteriorly convex dome shape. Then, as shown in FIG. 4, a planar cutting tool such as a razor blade 30 is introduced into the margin 29 of intralamellar pocket 26 through the opening formed by incision 18, and then sharpened leading edge 35 of blade 30 is passed in a direction perpendicular to optical axis A—A through the posteriorly protruding stromal mass of anterior lamellar portion 22, to excise stromal lenticule 32 from anterior lamellar portion 22. Lenticule 32 has relatively a thick center and progressively thinner edges, as established at the time of cutting by the shape of the posterial stromal mass of lamellar portion 22 and the planarity of the cut produced by the blade. Then blade 30 is withdrawn from the cornea, stromal lenticule 32 is removed, and the pressure at P is released to permit the altered cornea 31 to assume the anteriorly convex dome shape shown in FIG. 5.

Figure 5:
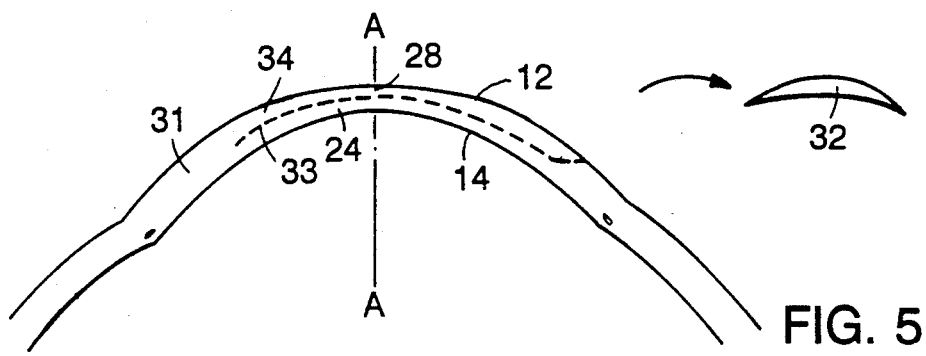

Once blade 30 and stromal lenticule 32 are removed, the stromal surface of the newly-shaped anterior lamellar portion 34 and the stromal surface of the posterior lamellar portion are in contact over substantially their entire extent, as indicated by broken line 33 in FIG. 5. Posterior surface 14 of the altered cornea 31 has substantially the same curvature as it had before the procedure, as shown in FIG. 1, and posterior lamellar portion 24 has substantially the same uniform thickness as it previously had. However, owing to removal of stromal lenticule 32, altered anterior lamellar portion 34 is thinner in a region 28 near axis A—A than toward its corneal margin. As a result the anterior curvature of altered cornea 31 is flatter than that of cornea 11 before alteration, i.e., the radius of curvature of at least the area of altered cornea 31 near the axis is greater than that of the cornea 11 before alteration, reducing its refractive power.

The method of alteration of corneal shape shown in FIGS. 1-5 can thus be used to correct myopia. The degree to which the refractive power of the cornea is reduced by the alteration depends upon the amount by which the radius of curvature of the anterior corneal surface 12 is altered; and the latter depends upon the shape of the removed stromal mass 32. By using different controlled pressures to posteriorly displace the lamellar portions different amounts before passing the cutting tool through the posteriorly projecting stromal mass, different shapes and thicknesses of stromal material can be removed, resulting in different refractive correction as required.

Figure 4A:
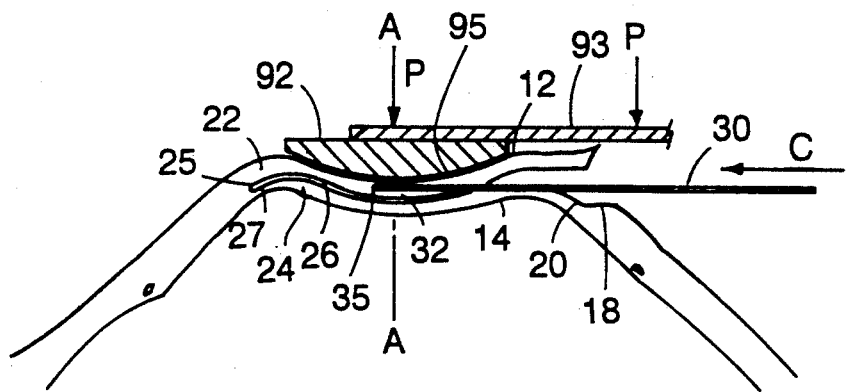
FIG. 4a is a sectional view as in FIG. 4, showing the use of a pressure member having a predetermined geometry.
Figure 7A:
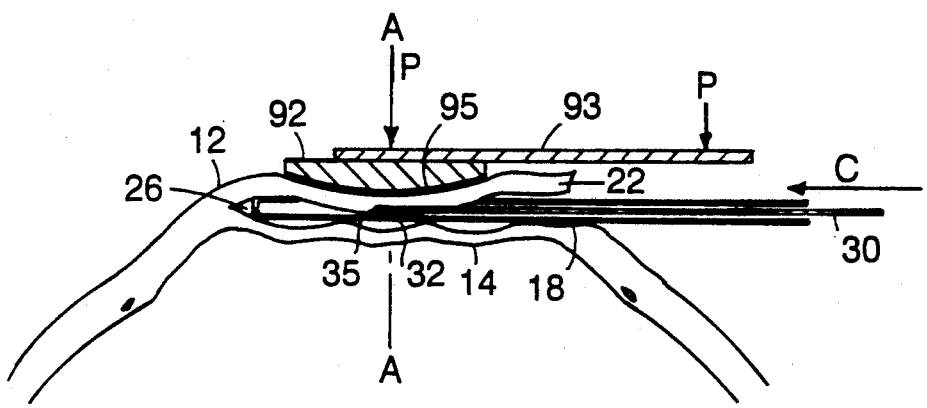
FIG. 7a is a sectional view as in FIG. 4a, showing the use of a cutter guide in conjunction with a pressure member having a predetermined geometry.

Control of the shape and dimensions of the removed stromal matter, and thus of the shape of the altered cornea, can for instance be obtained by the use of a pressure member 92 whose cornea-contacting surface 95 has a predetermined contour as shown in FIG. 4a. External pressure member 92 is manipulated by connecting brace 93. A set of pressure members 92 can be provided, each having a different, predetermined contour, and each resulting in a predetermined corneal alteration, the physician selecting the appropriate pressure member from the set.

Figure 6:
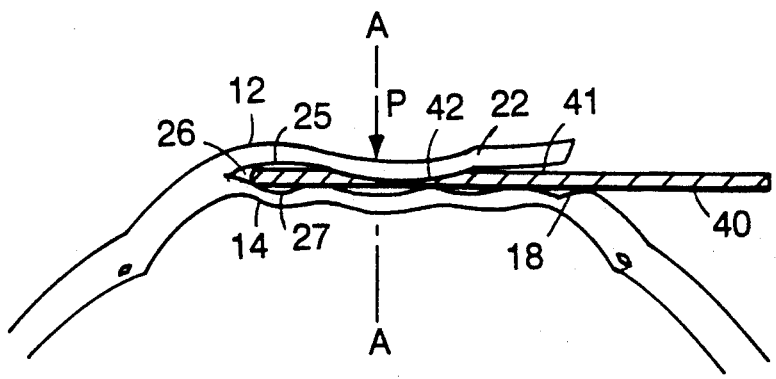
Figure 7:
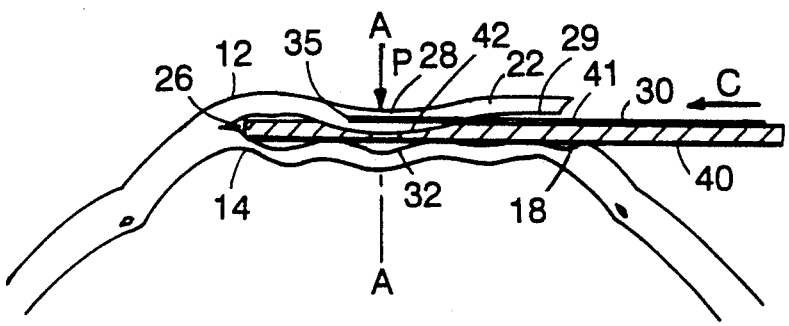
Figure 8:
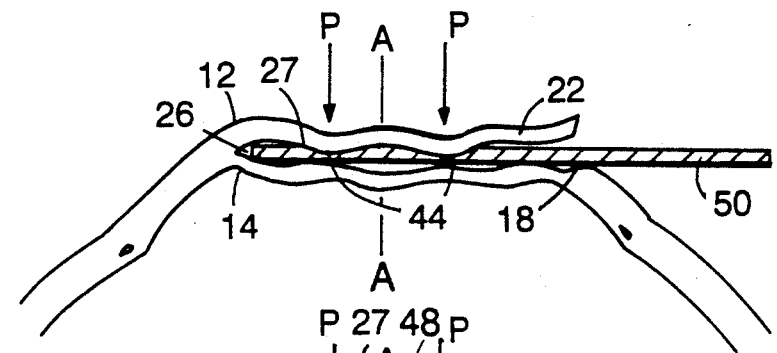
Figure 9:
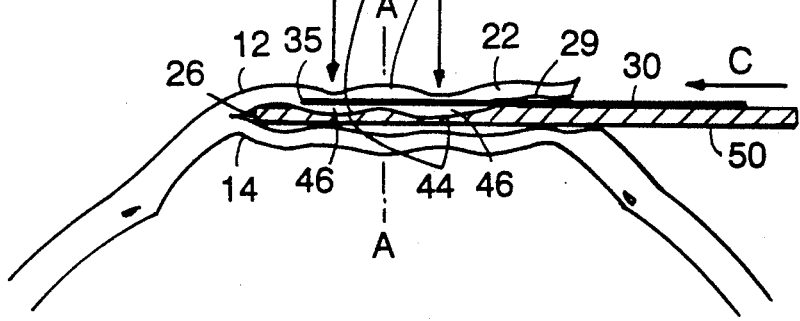
Figure 10:
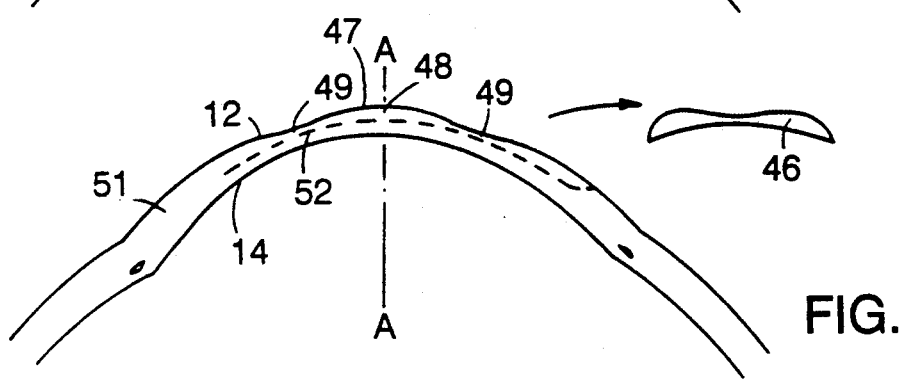

In the preferred embodiments of FIGS. 6-10, direct control of the shape and dimensions of the removed stromal matter, and thus of the shape of the altered cornea, can be obtained by inserting into the intralamellar pocket a die having an impression cavity of predetermined contour, forcing the anterior lamellar portion posteriorly into the cavity against its impression surface, and then making a planar cut to remove the portion of the stromal mass protruding into the cavity, as shown in FIGS. 6-7 and in FIGS. 8-10.

With reference now to FIG. 6, intralamellar die 40 is a generally spatula-shaped member having an impression surface 42. Intralamellar die 40 is inserted through the opening formed by incision 18 into intralamellar pocket 26, sliding between stromal surface 25 of anterior lamellar portion 22 and stromal surface 27 of posterior lamellar portion 24, with impression surface 42 facing anteriorly and centered upon optical axis A—A. Now pressure is applied posteriorly upon anterior corneal surface 12 as indicated by arrow P, to force a part of the stromal mass of anterior lamellar portion 22 into the cavity defined by impression surface 42. The pressure is applied so as to cause stromal surface 25 of anterior lamellar portion 22 to conform to impression surface 42 over substantially the whole extent of stromal surface 25, and to hold anterior lamellar portion 22 securely in place during the passing of the cutting tool through the stromal mass.

Then, as shown in FIG. 7, a cutting tool such as a blade 30 is introduced by way of incision 18 into the margin 29 of intralamellar pocket 26 and the advancing sharpened edge 35 of blade 30 is passed in a direction perpendicular to optical axis A—A through a plane adjacent to the anterior planar surface 41 of die 40, excising from the stromal mass of anterior lamellar portion 22 a stromal lenticule 32 whose shape is precisely determined by the plane of passing of blade 30 and by the contour of impression surface 42. Then blade 30 and die 40 are withdrawn, and stromal lenticule 32 is removed to yield an altered corneal shape as shown in FIG. 5. Impression surface 42 of die 40 is shown in FIGS. 6-7 as a part-spherical cavity, symmetrical about optical axis A—A when the die is properly positioned; such a die can be suitable for correction of simple myopia, and the degree of correction depends upon the radius of curvature and the depth at the optical axis of the cavity.

FIGS. 8-10 illustrate corneal alteration according to the invention using an intralamellar die 50 whose impression surface is designed for making a refractive correction of a hyperopic eye. As appears in FIG. 8, impression surface 44 of intralamellar die 50 defines an annular cavity, symmetrical about optical axis A—A when positioned so that impression surface 44 is centered upon optical axis A—A, whose depth is greatest at points spaced from its center. Thus, impression surface 44 includes a part-spherical anteriorly convex from whose center is at the optical axis A—A when the die is properly emplaced. Once intralamellar die 50 is properly emplaced, pressure is applied to anterior corneal surface 12, generally as described with reference to FIG. 6, as shown by, for example, arrows P. As in the example shown in FIGS. 6-7, this pressure causes a portion of the stromal mass of anterior lamellar portion 22 to protrude into the cavity of the impression surface and forces posterior stromal surface 25 of anterior lamellar portion 22 to conform with impression surface 44, holding the stromal mass securely in place during the passing of blade 30. Then the advancing sharpened edge 35 of blade 30 is passed through the posteriorly-protruding stromal mass of anterior lamellar portion 22, as shown in FIG. 9, excising from the stromal mass a stromal lenticule 46 whose shape is precisely determined by the plane of passing blade 30 and by the contour of impression surface 44. Then blade 30 and die 50 are withdrawn, and stromal lenticule 46 is removed. The resulting altered corneal shape is shown in FIG. 10.

Once blade 30 and stromal lenticule 46 are removed, the stromal surface of the newly-shaped anterior lamellar portion and the stromal surface of the posterior lamellar portion are in contact over substantially their entire extent, as indicated by broken line 52 in FIG. 10. Posterior surface 14 of the altered cornea 51 has substantially the same curvature as it had before the procedure, as shown in FIG. 1, and posterior lamellar portion 24 has substantially the same uniform thickness as it had before alteration. However, owing to removal of stromal lenticule 46, altered anterior lamellar portion 47 is thicker in the region 48 near optical axis A—A than in a surrounding midperipheral region 49 away from axis A—A, and thinner in surrounding midperipheral region 49 than lamellar portion 22 was before alteration. As a result the anterior curvature of altered cornea 51 is more steeply curved in the area near optical axis A—A than that of cornea 11 before alteration, i.e., the radius of curvature of at least the region of altered cornea 51 near the axis is less than that of the cornea 11 before alteration, increasing its refractive power.

With reference now to FIG. 11, there is shown generally at 60 preferred apparatus for carrying out the invention. Intralamellar die 62 is a generally rectangular flat member having a surface 64, facing the viewer in FIG. 11, which is to face anteriorly when die 62 is emplaced in the intralamellar pocket 26 as described above with reference to FIGS. 6–10. A portion of anterior surface 64 comprises impression surface 66, against which the stromal surface of anterior lamellar portion 22 of the cornea is to be forced when pressure is applied at P, as described above with reference to FIGS. 6, 8. The impression surface 66 of the die 62 shown in FIGS. 11, 12 comprises a part-spherical cavity 68 whose center of curvature is anterior to the cornea and substantially aligned with the optical axis A—A of the eye when intralamellar die 62 is properly emplaced within intralamellar pocket 26, as described generally above with reference to FIG. 6.

A blade 78, the edges of which are indicated in part by broken lines 72, 73 and in part by line 74, is slidably positioned within die 62 in a slot 76, the boundaries of which are indicated by broken lines 70, 79, 80 in FIG. 11. Slot 76 is substantially planar, and is situated parallel to and a narrow distance posterior to, anterior surface 64 of die 62. Slot 76 is dimensioned such that blade 78 slides freely without excessive chatter in directions lying generally in the plane of slot 76. Slot 76 is thus a cutter guide, ensuring that the cutting tool travels the appropriate path on its effective cutting stroke. Blade 78 has a width dimension such that blade 78 can oscillate in the plane of slot 76 within slot 76, that is, in the directions of arrows O. And blade 78 has a length dimension such that as it passes in the direction indicated by arrow C from a start position, in which its trailing edge 73 rests near the end of slot 76 indicated 79 in FIG. 11, to a finish position, in which its sharpened leading edge 77 rests near the end of slot 76 indicated 80 in FIG. 11, leading edge 77 makes an effective stroke across the circular opening 82 described by the intersection of slot 76 with impression surface 66. Blade 78 is simultaneously oscillated and advanced through the effective stroke by a motor-driven mechanism, described below with reference to FIGS. 12, 13.

With reference now to FIG. 12, there is shown a section thru the apparatus of FIG. 11 at XII—XII. Blade 78 is shown, as in FIG. 11, in a position intermediate the starting and finishing positions. Impression surface 66, including part-spherical cavity 68, as described above with respect to FIG. 11, appears in FIG. 12 as a part-circle, and it can be seen that as leading edge 77 makes an excursion across the opening 82 described by the intersection of slot 76 and impression surface 66, it generates a plane across the cavity.

The die, including the guide means, should be made as thin in its anterior-posterior dimension as can possibly be done while providing the required rigidity, and it should be made as narrow as can possibly be done while being at least as wide as the diameter of the impression surface and providing the required support for the cutter, so as to stretch and flex the corneal tissues on either side of the intralamellar pocket as little as possible. A suitable anterior-posterior dimension for the insertable portion of the apparatus, indicated for example as "a" in FIG. 12, is in the range 0.3 mm to 3 mm, and preferably about 1 mm. A suitable width dimension for the insertable portion of the apparatus, indicated for example as "b" in FIG. 11, is in the range 3 mm to 8 mm, and preferably in the range 4 to 6 mm. The correction resulting from an excision depends upon the thickness and configuration of the excised lenticule, that is, upon the shape and width of the impression surface and the depth of the cavity. For typical corrections for myopia, the cavity depth, that is, the anterior-posterior distance at the optical axis between the impression surface and the plane of the passing cutter, indicated as "d" in FIG. 12, can be in the range 5 microns to 200 microns, and more usually in the range 30 microns to 100 microns; and the width of the cavity at the edge formed by the intersection of the impression surface and the cutter, indicated as "c" in FIG. 11, can be in the range 3 mm to 6 mm, and more usually in the range 4 mm to 5 mm. Typically, for correction of myopia, for example, the ratio of the depth "d" to the width "c" is in the range 1:30 to 1:200. The die can be made of metal, such as, for example, a surgical stainless steel, or it can be made, for example, of a rigid plastic material or of a material made rigid by metal reinforcement. The blade is conveniently a commerical stainless steel razor blade, as thin as practicable, although any suitably thin and sharp blade can be used. The blade must additionally be sufficiently rigid that it does not wander from a planar path, and preferably the blade is capable of making cuts that are predictable and repeatable within a tolerance of about 5 microns or less. More preferably the blade is a gem stone blade, such as a sapphire or ruby or diamond blade, to provide a highly predictable and reliable cut.

As will be appreciated by one skilled in opththalmic surgery, the overall shape of the insertable portion of the die, including the guide means, should be contoured so as to reduce damage to corneal tissues on either side of the intralamellar pocket. The peripheral edge of the die and cutter guide should be rounded, for example, and the edge and surfaces should be smooth.

Apparatus 60 is further provided with means, indicated generally at 90 in FIG. 12, for applying a force to displace posteriorly onto impression surface 66 an anterior lamellar portion 22 of a cornea 11 to be altered, as described generally above with reference to FIG. 6. Force applying means 90 include a pressure member 92, mounted by means of a connecting brace 93 and thumbscrews 96 to threaded posts 94, of which only posts 94 are shown in FIG. 11. Turning thumbscrews 96 causes pressure member 92 to move in the direction of the optical axis, toward or away from impression surface 66 of die 62. When die 62 is emplaced within the intralamellar pocket, and impression surface 66 is overlain anteriorly by the anterior lamellar portion of the cornea as described generally above with reference to FIGS. 6–9, pressure member 92 is moved posteriorly toward die 62 until pressure surface 95 of pressure member 92 presses against the anterior surface of the anterior lamellar portion of the cornea, forcing a posterior stromal mass of the anterior lamellar portion to protrude posteriorly into cavity 68. Pressure surface 95 is configured to generally complement impression surface 66, including cavity 68, such that when pressure is so applied the stromal surface of the anterior lamellar portion contacts impression surface 66 over substantially the entire extent of impression surface 66. Sufficient force is applied to hold the anterior lamellar portion of the cornea securely in place during passage of sharpened edge 77 of blade 78 through the porteriorly protruding stromal mass of the anterior lamellar portion of the cornea.

Impression surface 66 is shown by way of example in FIGS. 11, 12 as comprising a part-spherical cavity 68 whose center of curvature is situated on the optical axis of the eye and anterior to the cornea when the die is emplaced within the intralamellar pocket; and pressure surface 95 of pressure member 92 is shown by way of example in FIG. 12 as comprising a part-spherical posteriorly convex surface. Apparatus so configured can be used for correcting simple myopia, as described above with reference to FIGS. 6-7. The impression surface and its complementing pressure surface can have other configurations as required for making other corrections, such as, for example, simple hyperopia, as described above with reference to FIGS. 8-10. A series of dies and pressure members can be produced, each having an impression surface and a complementing pressure surface for a particular prescribed correction.

It will be appreciated that, as the cutter is passed through the stromal mass, the stromal mass will be displaced owing to the finite thickness of the cutter: A rigid and unyielding configuration of the apparatus as configured for example in FIGS. 11 and 12 could subject the stromal mass to increased compression between pressure surface 95 and impression surface 66 as the cutter passes through. Preferably, pressure surface 95 is configured to yield to the displacement of the stromal mass while maintaining pressure on the stromal mass during cutting, to permit a more rapid and smooth passage of the cutter than would be permitted by a rigid or unyielding configuration. In one embodiment, pressure member 92 is resiliently mounted on die 62 so that it provides a resiliently urging force displacing the anterior lamellar portion of the cornea posteriorly onto the impression surface. Such resilient mounting can be provided, for example, by making connecting brace 93 or threaded posts 94 of a flexible material. More preferably, as shown in FIG. 12a, pressure member 92 is pivotally mounted on posts 94 by, for example, providing brace 93 with a hinge 93a, so that it can pivot toward and away from impression surface 66, and is resiliently urged toward impression surface 66 by coil spring 97, stretched between connecting brace 93 and die surface 64. Most preferably, however, pressure member 92 is rigidly mounted on die 62, and pressure surface 95 is made of a deformable material capable of holding the stromal mass securely in place, with the stromal surface of the anterior lamellar portion in contact with the impression surface 66, as the cutter passes. Suitable deformable materials include, for example, captured gel, cellular foam, or membrane enclosed fluid.

As is suggested for example in FIG. 11, pressure surface 95 of pressure member 92 should be somewhat larger than impression surface 66, so that at least a portion of the margin of the pressure member extends radially beyond the margin of the impression surface; the extended pressure member margin can help to keep the anterior corneal lamella in more secure contact with the impression surface margin, insuring an accurate and smooth transition at the edge of the cut in the tissue remaining on the anterior lamella in the corrected cornea. An improved corrective result for myopia can be obtained by providing an impression surface 66' having a composite curvature, as shown in diagrammatic sectional view in FIG. 19. Such a composite curvature provides for a gradual transition between the part-spherical portion of the impression surface and the marginal portion, so that no abrupt edge is formed in the excised stromal lenticule, and, as a result, no abrupt change appears at the margin of the altered portion of the corrected cornea. Impression surface 66' includes part-spherical cavity 266 whose center of curvature "x" is situated on the optical axis of the eye and anterior to the cornea when the die is emplaced within the intralamellar pocket. The margin 267 of impression surface 66' includes curvature 268, so that cutter 78 passes through the stromal mass in a plane 269 that is substantially tangential to impression surface 66' at the edge 270 of the margin 267 of impression surface 66'. Curvature 268, as shown for example in FIG. 19, can be a section of a toroid formed by the rotation of a circle having a center t about the optical axis. The excised stromal lenticule 232 has a very gradually tapered margin 233, which can result in less distortion at the periphery of the correction than can be provided by excision of a part-spherical lenticule whose surfaces are substantially nontangent at the lenticular edge.

Figure 17A:
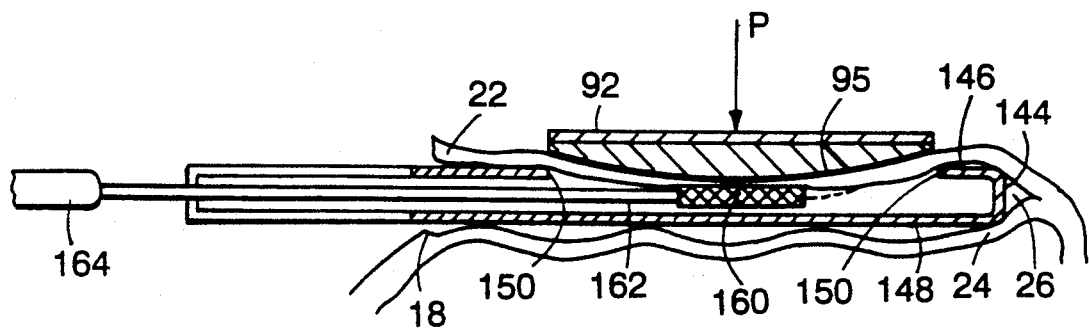
FIG. 17a is a sectional view through 17a—17a in FIG. 17, showing the use of a burr-type cutting tool in a cutter guide in conjunction with a pressure member having a predetermined geometry.

Apparatus 60 is shown in FIGS. 11, 12 as comprising die 62 and cutter guide means, including slot 76, as an integral part thereof. It will be appreciated that the cutter guide can also be provided as, for example, a slotted frame removable from the die body. Such a cutter guide can be adapted to be used with any of the various dies, so that one cutter guide serves for use with a set of dies. Moreover, such a cutter guide can be used to support and guide a cutter when the method not employing a die is used, as described generally above with reference to FIGS. 1-5, and to guide other types of cutters, as described below with reference to FIGS. 16-18.

Now, with reference to FIGS. 11-14, blade 78 is oscillated and advanced through its effective stroke as follows. Bracket 190 is provided to hold blade 78 by pressure-fitting posterior edge 73 of blade 78 about midway the width of blade 78 into slot 192 in bracket 190. Drive wheel 194 is provided on one face with an eccentrically located pin 104 and is affixed on the opposite face to an end of drive shaft 196. Drive shaft 196 is journaled at 198 in frame member 100, which is affixed to die 62. Drive shaft 196 is rotated, for example as shown by arrow R in FIG. 14, by an electric motor, not shown in the figures, coupled to another end of drive shaft 196. Bracket 190 is provided with a follower slot 102, disposed perpendicular to slot 192 and thus perpendicular to the plane of blade 78, which slidably engages pin 104. As drive wheel 194 rotates, pin 104 revolves about the center of rotation and causes blade 78 to oscillate as shown by arrows O.

Preferably a motor (not shown in FIGS. 11-14), such as an electric motor, both oscillates the blade and drives the blade through its effective cutting stroke, to achieve a desired precision and repeatability in the shape and dimensions of the corrected cornea. Drive shaft 196 in FIG. 12 is driven in the direction of arrow C to move blade 78 through its effective cutting stroke by, for example, a worm-gear mechanism coupled to the rotation of the motor. Preferably, the cutter will complete its advance through its effective stroke in a time of ten seconds or less, and more preferably in less than five seconds, and the blade should advance at a constant rate, to minimize irregularities in the resulting surface.

Alternative cutter and cutter guide configurations can be used according to the invention.

Figure 15:
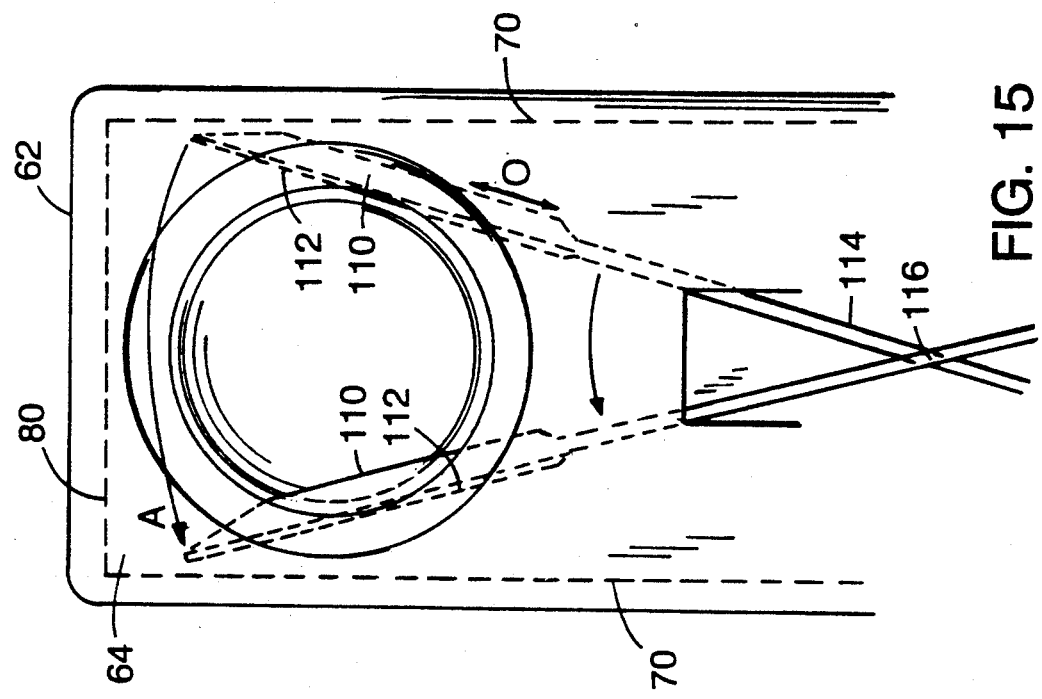

For example, as shown in FIG. 15, the cutter can be a lance-shaped blade 110, having sharpened leading edge 112, which oscillates generally in the direction of its length, as shown by arrows O, and advances across the opening 82 in cutter guide 62 by sweeping through an arc as shown generally by arrow A. Advantageously, oscillations O of lance-shaped blade 110 are generated by mechanical means (not shown), and the sweep through arc A is effected either free-hand or by manual or mechanical manipulation of handle 114 about a pivot, shown diagramatically at 116 in FIG. 15.

One having knowledge of opthalmic surgical cutting instruments and their use will appreciate that the oscillatory motion of the blade is not essential but that generally better results are obtained by oscillating the cutting edge in the plane of cutting in a direction orthogonal to the direction of the effective cutting stroke. The cutting edge preferably oscillates at a frequency in the range between about 5000 cycles per minute and about 50,000 cycles per second, and most preferably about 15,000 cycles per minute, and at an amplitude in the range between about 0.004 inch and about 0.200 inch, and most preferably about 0.090 inch.

While the oscillatory motion of the blade must as a practical matter be driven by some mechanical means such as a motor, the effective cutting stroke need not be motor-driven, but can be effected by hand by the surgeon, but manipulation of the blade by hand is less preferred owing to irregularity and lack of precision in the resulting cut and, consequently, in the resulting corrected cornea.

The device of the invention is used generally as described above with reference to FIGS. 1-9. The user determines the type and degree of correction required, and then, if the use of a die is desired, the user selects a die having the appropriately configured impression surface. Generally the surgery is performed according to customary corneal surgical practice, and, as will be evident to one skilled in the ophthalmic art, some steps in a complete procedure for performing the corneal alteration are omitted from the description that follows. After the eye is prepared and a surgical field is established on the cornea, a peripheral chordal incision is made and an intralamellar pocket is formed as described generally above with reference to FIGS. 1-3. Advantageously the incision is made no longer than necessary to permit the device to pass through it into the pocket. Then the selected die, preferably including a cutter guide, is inserted through the incision onto the intralamellar pocket and the impression surface is centered upon the optical axis of the eye as described above with reference to FIGS. 6, 8. Then force is applied, for example, by moving a selected pressure member posteriorly against the anterior corneal surface, to cause a posterior stromal mass of the anterior lamellar portion of the cornea to protrude posteriorly into the cavity of the impression surface of the die as described above with reference to FIGS. 6, 8. Once the stromal surface of the anterior lamella is in secure and substantial contact with the impression surface of the die, the blade is oscillated and advanced through its effective cutting stroke, as described above with reference to FIGS. 7, 9 and 11-14. Once the excision of the stromal lenticule is complete, the posteriorly directed force on the anterior corneal surface is relieved by, for example, moving the pressure member anteriorly, and the die is removed from the intralamellar pocket, with the stromal lenticule contained within the cavity of the impression surface. Any air or fluid that may have entered the pocket during the procedure is removed so that the newly-formed stromal surface of the anterior lamellar portion of the cornea substantially contacts the stromal surface of the posterior lamellar portion of the cornea, so that the anterior surface of the cornea assumes its new curvature. Finally the incision is closed by, for example, suturing or application of a bioadhesive.

Figure 16:
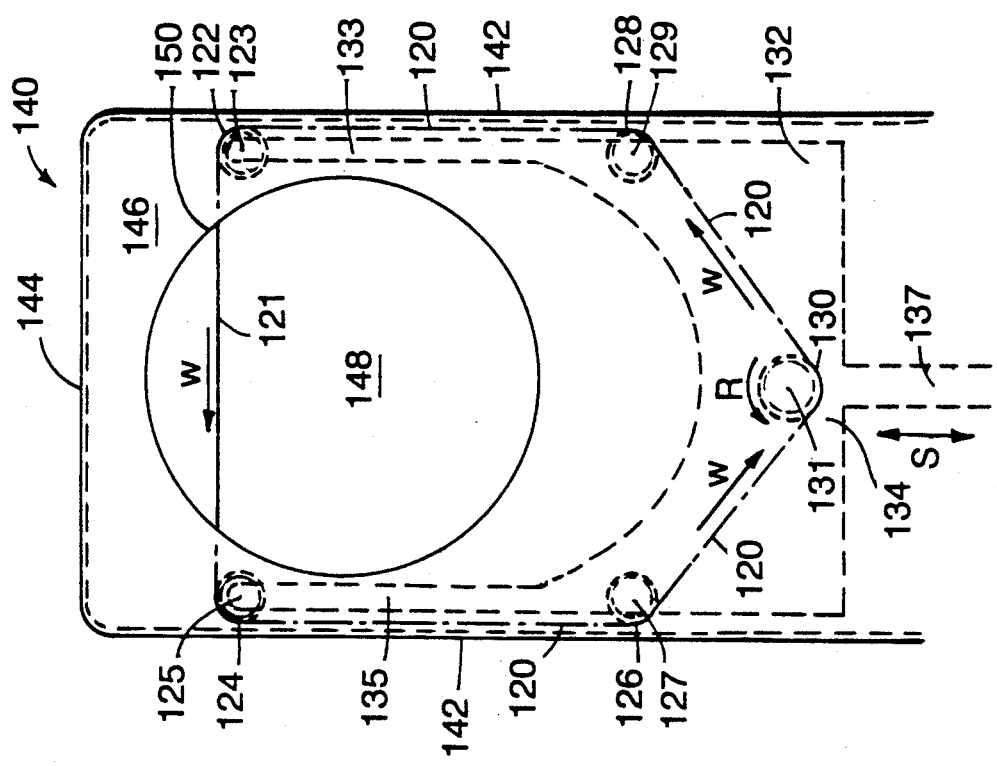

Alternatively, the cutter can have the form of a fine gauge wire, held taught in a generally transverse orientation with respect to the direction of its effective stroke, as shown for example in FIG. 16. With reference now to FIG. 16, wire 120 is configured as a closed loop, and passed around idler wheels 122, 124, 126, 128 and drive wheel 130, which are rotatably mounted on carrier 132. Carrier 132 is generally Y-shaped, having arm portions 133, 135, body portion 144, and handle portion 137. Idler wheels 122, 124 are rotatably mounted on axles 123, 125 respectively on the ends of arm portions 133, 135; idler wheels 126, 128 are rotatably mounted on axles 127, 129 respectively on the bases of arm portions 135, 133; and drive wheel 130 is rotatably mounted on body portion 144 near handle portion 137 of carrier 132. A cutter guide, shown in part at 140 in FIG. 16, is shaped and dimensioned to contain carrier 132, such that carrier 132 together with the wheels mounted on it can slide freely in the direction of arrows S within cutter guide 140. Cutter guide 140 has an upper wall 146 having a circular opening 150, a lower wall 148, side walls 142, and end wall 144.

For use, cutter guide 140 is inserted into intralamellar pocket 26, with upper wall 146 of cutter guide 140 directed anteriorly and with the center of circular opening 150 located on the optical axis of the cornea. Then carrier 132 is moved to a starting position within cutter guide 140, in which wheels 122, 124 are near end wall 144, and the transverse portion 121 of wire 120 passing between wheels 122, 124 does not intersect circular opening 150. Then anterior lamellar portion 22 of cornea 12 is displaced posteriorly, generally as described above with reference to FIG. 6, so that a posterior stromal mass of anterior lamellar portion 22 projects through opening 150 into cutter guide 140. Then carrier 132 is moved in a direction S generally away from end wall 144, drawing transverse portion 121 of wire 120 in an effective stroke forming a planar incision through the posteriorly projecting portion of the stromal mass. Then the cutter guide, containing the cutter (carrier, wheels, and wire), and the excised portion of the stromal mass are removed from the pocket. Preferably, as a practical matter, drive wheel 130 is caused to rotate as shown by arrow R, by mechanical means (not shown), so that wire 120 travels continually around wheels 122, 124, 126, 130, and 128, as shown by arrows W. Wire 120 must be sufficiently fine and sufficiently tightly drawn between wheels 122, 124 that it effectively forms a cutting edge as it passes through the stromal mass; and it preferably is of a material that has high tensile strength and that endures repeated flexing as it passes around the wheels. It will be appreciated that a wire cutter can be used with a die as well as a cutter guide, and that the carrier and the cutter guide of FIG. 16 can be adapted to accommodate a die or any one of a set of dies for use in making various different optical alterations, as described generally above.

Alternatively, a cutter guide like that shown generally at 140 in FIG. 16 can be used with other cutters, such as a rotating burr, as shown for example in FIG. 17, or such as a beam of laser energy, as shown for example in FIG. 18.

Referring to FIG. 17, a cutter guide 140, generally as described with reference to FIG. 16, is configured to permit burr 160, carried on rotating wand 162, to be moved between walls 146, 148 within cutter guide 140 end-to-end, as shown generally by arrows E, and in an arc as shown generally by arrows B. Wand 162 is advantageously rotated as shown by arrow R by mechanical means such as, for example, a motor, shown in part diagramatically at 64; the movements E and B of burr 160 can be carried out free-hand, or can be produced by mechanical means (not shown).

Similarly, referring to FIG. 18, a cutter guide 140 is configured to allow the passage therewithin of a beam 180 of laser energy. As one knowledgeable in laser surgery will appreciate, the laser can be of a UV type, whereby collagen in tissues encountered by the beam is disrupted; or it can be of an IR type, whereby tissues encountered by the beam are destroyed by heat; or it can be of a YAG type.

In either the burr-type or the laser-type cutter, the cutter guide is placed into the lamellar pocket 26 and then the anterior lamellar portion of the cornea is posteriorly displaced through opening 150 into the cutter guide, as described above with reference to FIG. 16, and then the burr or the laser is used to break up the tissues of the stromal mass that project posteriorly into the interior of the cutter guide. Both the burr-type cutter and the laser-type cutter break up the tissues in their path, rather than making a planar cut as with the blade-type or wire-type cutters, and so the burr and the laser types of cutters are not as readily adapted for use with a die. The form taken by the altered cornea can be determined to some extent when using a burr-type or laser-type cutter even without the use of a die by selecting an appropriate shape or degree of pressure applied onto the anterior corneal surface when posteriorly displacing the anterior lamellar portion, as described above generally with reference to FIGS. 1-4. This is illustrated in respect of the burr-type cutter in FIG. 17a.

As will be appreciated from the foregoing description of the apparatus according to the invention, in each configuration of the die and the cutter guide the apparatus is in the form of a cantilever whose projecting end is insertable into the blind intrastromal pocket of the cornea to be altered, and in each configuration the cutter is introduced into the stromal pocket by way of the same incision through which the die or cutter guide is inserted. The cutter is operated from near the base of the cantilever, and the cutter does not pass through the anterior corneal surface at any point. In particular, where the cutter is a blade as in the preferred embodiment illustrated for example in FIGS. 6-9 and 11-14, the effective stroke is in a direction away from the base of the cantilever toward the projecting end. As is shown and described below, with reference to FIGS. 20 and 20a, preferably the cantilever is supported at its base by a handle, with which the surgeon holds and manipulates the apparatus.

The apparatus is preferably contoured to be handheld, and readily manipulable by the ophthalmic surgeon. For convenience in use the apparatus can be provided with a handle, as illustrated for example in FIGS. 20 and 20a. Handle 200 is dimensioned and configured to be comfortable in the surgeon's hand, and to allow manipulation of the apparatus, which can include die, cutter guide, and cutter, through the steps of insertion, excision, and removal. The handle can, according to the practice of the surgeon, most conveniently be aligned with plane of the cutting stroke, as shown for example in FIG. 20, or inclined with respect thereto, as shown for example in FIG. 20a; and the handle position can be either fixed or adjustable over a suitable range. Most conveniently, the handle can be a hollow shell made, for example, of a sturdy polymer, and can be configured and dimensioned so that the motor can be contained within the handle, as shown for example in FIG. 20a. Motor 202 in FIG. 20a is an electric motor, and can be powered from standard line current or by batteries 204, as appropriate for the particular motor. Driveshaft 206 of motor 202 is linked to driveshaft 196 by way of a suitable conventional linkage 208, which can include, for example, a worm-gear mechanism for advancing the blade through its effective stroke and an eccentric coupling for oscillating the blade, as described above with reference to FIGS. 11-14.

Other embodiments are within the following claims.

I claim:

1. A method for surgically altering the cornea of an eye, comprising
    forming a pocket in the stroma of said cornea, said pocket being situated between an anterior lamellar portion of said cornea and a posterior lamellar portion of said cornea,
    posteriorly displacing said anterior lamellar portion to form a posteriorly protruding mass of corneal stroma of said anterior lamellar portion,
    excising a part of said posteriorly protruding mass, and
    removing from said pocket said excised part of said posteriorly protruding mass.

2. The method of claim 1 whereby the step of forming a pocket comprises making an incision in said cornea and separating by dissection said anterior lamellar portion of said cornea from said posterior lamellar portion of said cornea.

3. The method of claim 2 whereby said incision comprises a peripheral chordal incision.

4. The method of claim 3 wherein said impression surface comprises a part-spherical surface whose center of curvature is located anterior to said impression surface when said die is inserted into said pocket.

5. The method of claim 3 wherein said impression surface comprises a part-spherical surface whose center of curvature is located posterior to said impression surface when said die is inserted into said pocket.

6. The method of claim 2, said method further including inserting a die into said pocket, said die having an impression surface facing anteriorly when said die is so inserted, the step of posteriorly displacing said anterior lamellar portion to form a posteriorly protruding mass of corneal stroma of said anterior lamellar portion comprising forcing a portion of said posteriorly protruding mass against a portion of said impression surface,
    said method further including removing said die from said pocket after said excising.

7. The method of claim 2 or 6, said method further comprising inserting a cutter guide into said pocket prior to said excising, employing said cutter guide during said excising, and removing said cutter guide after said excising.

8. The method of claim 6, said die further comprising a cutter guide.

9. The method of claim 1 wherein said excising comprises passing a cutter through said posteriorly protruding mass of corneal stroma.

10. The method of claim 1 wherein said excising comprises passing a cutting edge through said posteriorly protruding mass of corneal stroma.

11. The method of claim 8 wherein said cutting edge describes a plane during said passing through said posteriorly protruding mass of corneal stroma.

12. The method of claim 11 wherein said cutting edge oscillates substantially in said plane during said passing through said posteriorly protruding mass of corneal stroma.

13. A method for surgically altering the cornea of an eye, comprising
   forming a pocket in the corneal stroma of said cornea, said pocket being situated between an anterior lamellar portion of said cornea and a posterior lamellar portion of said cornea,
   inserting a die into said pocket, said die having an impression surface, said impression surface facing anteriorly when said die is inserted into said pocket,
   forcing a posterior portion of the stromal mass of said anterior lamellar portion against a portion of said impression surface in said die, and
   excising a posterior part of said posterior portion of said stromal mass, and removing from said pocket said die and said excised part.

14. The method of surgery of claim 1 wherein the excising of said part of the posteriorly protruding mass of corneal stroma is performed using apparatus comprising the combination of
   a cutter guide assembly having at its distal end a cutter guide sized and constructed for insertion through an incision into said pocket of the cornea of the eye into alignment with the portion of the cornea to be altered,
   said cutter guide assembly having a proximal portion arranged to remain outside of the eye,
   means for forming a posteriorly protruding mass of the anterior lamellar portion adjacent said cutter guide, and
   a cutter having actuating means located proximally from said cutter guide, and cutting means, actuated by said actuating means, extending into said cutter guide to excise a part of said posteriorly protruding mass, said cutting means confined within said cutter guide in a manner that preserves optical properties of the residual corneal tissue.

15. The method of claim 14 wherein said means for forming the posteriorly protruding mass comprises an exterior pressure surface having a preformed contour constructed and arranged to press inwardly against the cornea, to provide a desired shape to the posterior side of the anterior lamellar portion.

16. The method of claim 15 wherein said pressure surface is made of a yielding material.

17. The method of claim 16 wherein said yielding material comprises a captured gel.

18. The method of claim 16 wherein said yielding material comprises cellular foam.

19. The method of claim 16 wherein said yielding material comprises a membrane enclosed fluid.

20. The method of claim 14 wherein said means for forming the posteriorly protruding mass comprises a die associated with said cutter guide, said die having an impression surface arranged to face anteriorly when said die is so inserted, said impression surface adapted to be contacted by and provide a desired shape to the posterior side of the anterior lamellar portion.

21. The method of claim 20 wherein said die further comprises a generally planar die surface, said planar die surface being generally parallel to said impression surface.

22. The method of claim 21 wherein the anterior-posterior dimension of said die, as measured between said impression surface and planar die surface, is in the range 0.3 mm to 3 mm.

23. The method of claim 22 wherein said anterior-posterior dimension is about 1 mm.

24. The method of claim 14 wherein said means for forming the posteriorly protruding mass comprises
   an exterior pressure member comprising a pressure surface having a preformed contour constructed and arranged to contact the anterior surface of the cornea, said pressure surface having a peripheral margin and
   a die constructed and arranged to be inserted in the pocket, said die having an impression surface arranged to face anteriorly when said die is so inserted, said impression surface adapted to be contacted by the posterior side of the anterior lamellar portion, said impression surface having a peripheral margin,
   whereby movement of said pressure surface posteriorly bringing a posteriorly projecting portion of the anterior lamellar portion into contact with said die impression surface, provides a desired shape to the posterior side of the anterior lamellar portion.

25. The method of claim 24 wherein a portion of said margin of said pressure surface extends radially beyond said margin of said impression surface.

26. The method of claim 24 wherein said pressure member is configured to yield to displacement of the stromal mass during passage of the cutter therethrough.

27. The method of claim 1 in which said part of said posteriorly protruding mass is excised employing an apparatus comprising the combination of
   a cutter guide assembly having at its distal end a cutter guide sized and constructed for placement in said pocket, said cutter guide adapted for insertion into the pocket by way of an incision in the anterior surface of the cornea,
   said cutter guide assembly having a proximal portion arranged to remain outside of the eye, and
   a cutter for excising a posterior portion of a posterior stromal mass of the anterior lamellar portion, said cutter having actuating means located proximally from said cutter guide and cutting means sized and constructed for placement in the pocket and adapted for insertion into the pocket by way of the incision through which the cutter guide is inserted, said cutter means, actuated by said actuating means, extending into said cutter guide and confined with said cutter guide in a manner that preserves optical properties of the residual corneal tissue,
   said cutter guide assembly and said cutter adapted to cooperate in guiding said cutter means through a prescribed effective stroke during said excising.

28. The method of claim 27 wherein said means for forming a posteriorly protruding mass comprises a die constructed and arranged for placement in the pocket formed in the stroma of the cornea, a portion of said die adapted to be placed between the anterior lamellar portion of the cornea and the posterior lamellar portion of the cornea.

29. The method of claim 28 wherein said die has an impression surface, said impression surface being adapted to face anteriorly when said die is placed in the pocket.

30. The method of claim 20 or 29 wherein said impression surface comprises a part-spherical surface whose center of curvature is located anterior to said impression surface when said die is inserted into the pocket.

31. The method of claim 20 or 29 wherein said impression surface comprises a part-spherical surface whose center of curvature is located posterior to said impression surface when said die is inserted into the pocket.

32. The method of claim 20 or 29 wherein said impression surface comprises an aspherical surface.

33. The method of claim 27 or 28 wherein said cutting means comprises a cutting edge.

34. The method of claim 33 wherein said edge is arranged to described a plane during passing of said edge through the posterior portion of the anterior lamellar portion of the corneal stroma.

35. The method of claim 34 wherein said edge is adapted to oscillate substantially in said plane during said passing through the posteriorly protruding mass of corneal stroma.

36. The method of claim 33 wherein said edge is straight.

37. The method of claim 33 wherein said cutting edge comprises a gem stone blade.

38. The method of claim 37 wherein said gem stone blade comprises a diamond blade.

39. The method of claim 27 or 28 wherein said cutting means comprises a length of wire.

40. The method of claim 39 wherein said length of wire comprises a continuous loop.

41. The method of claim 40, further including means for moving said wire in a direction along its length during an effective cutting stroke.

42. The method of claim 14, 27 or 28 wherein said cutting means comprises a burr, and said apparatus further comprises means for rotating said burr.

43. The method of claim 14, 27 or 28 wherein said cutting means comprises means to direct laser energy, and said apparatus further comprises means for generating said laser energy.

44. The method of claim 20 or 28 wherein said die is configured and dimensioned so that said insertable portion of said die can be inserted into the pocket without damage to the stroma.

45. The method of claim 14, 27 or 28 wherein said apparatus further comprises a handle.

46. The method of claim 45 wherein said handle comprises a hollow shell, and said apparatus further comprises a motor contained within said handle, said motor being coupled to said cutter to advance said cutter through its effective cutting stroke.

47. The method of claim 27 wherein said cutter guide is adapted to prevent passage of said cutter beyond the peripheral edge of said cutter guide, to prevent said cutter from contacting the surrounding stroma.

* * * * *